(12) United States Patent
Esbech

(10) Patent No.: US 11,911,206 B2
(45) Date of Patent: Feb. 27, 2024

(54) CALIBRATION OBJECT FOR AN X-RAY SYSTEM

(71) Applicant: NEWTON2 APS, Herlev (DK)

(72) Inventor: Bo Esbech, Værløse (DK)

(73) Assignee: NEWTON2 APS, Herlev (DK)

( * ) Notice: Subject to any disclaimer, the term of this patent is extended or adjusted under 35 U.S.C. 154(b) by 485 days.

(21) Appl. No.: 17/270,152

(22) PCT Filed: Aug. 23, 2019

(86) PCT No.: PCT/EP2019/072547
§ 371 (c)(1),
(2) Date: Feb. 22, 2021

(87) PCT Pub. No.: WO2020/039055
PCT Pub. Date: Feb. 27, 2020

(65) Prior Publication Data
US 2021/0315537 A1    Oct. 14, 2021

(30) Foreign Application Priority Data

Aug. 23, 2018 (DK) .............. PA201870547

(51) Int. Cl.
| A61B 6/00 | (2006.01) |
| G06T 7/80 | (2017.01) |
| A61B 6/03 | (2006.01) |
| B32B 3/26 | (2006.01) |
| B32B 17/06 | (2006.01) |
| B32B 37/12 | (2006.01) |

(Continued)

(52) U.S. Cl.
CPC .............. A61B 6/582 (2013.01); A61B 6/032 (2013.01); A61B 6/4085 (2013.01); B32B 3/266 (2013.01);

(Continued)

(58) Field of Classification Search
CPC ....... A61B 6/582; A61B 6/032; A61B 6/4085; A61B 6/4417; A61B 6/501; A61B 6/587;
(Continued)

(56) References Cited

U.S. PATENT DOCUMENTS

2008/0093544 A1* 4/2008 Wang ............... A61B 6/583
250/252.1
2009/0190723 A1   7/2009 Jang et al.
(Continued)

FOREIGN PATENT DOCUMENTS

| WO | 2016139347 A1 | 9/2016 |
| WO | 2017211955 A1 | 12/2017 |

OTHER PUBLICATIONS

Cho, Y., "Accurate technique for complete geometric calibration of cone-beam computed tomography systems", Medical Physics, vol. 32, No. 4, pp. 968-983, Apr. 2005.
(Continued)

*Primary Examiner* — Courtney D Thomas
(74) *Attorney, Agent, or Firm* — BUCHANAN INGERSOLL & ROONEY PC

(57) ABSTRACT

Disclosed is a calibration object for an x-ray system and an optical system, the calibration object comprising: a first part made of a first material having a matte surface, the first material having a first attenuation coefficient of x-rays; a second part made of a second material having a second attenuation coefficient of x-rays different from the attenuation coefficient of the first material; wherein the first part is attached to the second part so that one or more features are detectable by one or more optical cameras.

18 Claims, 2 Drawing Sheets

(51) Int. Cl.
   *B32B 38/10* (2006.01)
   *C23F 1/00* (2006.01)
(52) U.S. Cl.
   CPC ............ *B32B 17/061* (2013.01); *B32B 37/12* (2013.01); *B32B 38/10* (2013.01); *C23F 1/00* (2013.01); *G06T 7/80* (2017.01); *B32B 2311/00* (2013.01); *B32B 2315/08* (2013.01); *B32B 2535/00* (2013.01); *G06T 2207/10116* (2013.01); *G06T 2207/30201* (2013.01)
(58) Field of Classification Search
   CPC ....... A61B 6/583; B32B 3/266; B32B 17/061; B32B 37/12; B32B 38/10; B32B 2311/00; B32B 2315/08; B32B 2535/00; C23F 1/00; G06T 7/80; G06T 2207/10116; G06T 2207/30201
   See application file for complete search history.

(56) References Cited

U.S. PATENT DOCUMENTS

| | | |
|---|---|---|
| 2013/0230150 A1 | 9/2013 | Weiss |
| 2014/0119510 A1 | 5/2014 | Wang et al. |
| 2018/0014809 A1 | 1/2018 | Lin et al. |
| 2018/0070902 A1 | 3/2018 | Lin et al. |

OTHER PUBLICATIONS

Danish Search Report dated Feb. 1, 2019, issued in corresponding Danish Patent Application No. PA 2018 70547. (8 pages).
International Search Report (PCT/ISA/210) and Written Opinion (PCT/ISA/237) dated Nov. 4, 2019, by the European Patent Office as the International Searching Authority for International Application No. PCT/EP2019/072547.

* cited by examiner

CALIBRATION OBJECT FOR AN X-RAY SYSTEM

TECHNICAL FIELD

Disclosed herein is a calibration object and a method for producing the calibration object for use with an x-ray system. More particularly, the disclosure relates to a calibration object that can be used to calibrate both an x-ray system and one or more optical systems.

BACKGROUND

In any medical imaging system, it is important to calibrate the system. For X-ray systems this typically means determining the relative position of the X-ray source and sensor. In order to perform this calibration, a calibration object is used. The calibration object needs to provide contrast in X-ray, meaning that certain parts of the calibration object needs to absorb the x-rays, while other parts needs to let them pass. In practice, this requires some object consisting partly of metal, which will absorb most of the x-rays impacting it, and partly of some other material such as plastics, glass, carbon fibre, or some other material which will let most of the x-rays through.

The paper "Accurate technique for complete geometric calibration of cone-beam computed tomography systems" describes an object consisting of a plastic tube with embedded steel balls. Placing the steels balls with high accuracy is inherently difficult, so each manufactured calibration object usually requires an associated data file.

Some x-ray systems, including many cone beam computed tomography (CBCT) systems also have optical systems such as for example face scanners. Traditionally, these optical systems have been calibrated using a different calibration routine than that used for the x-ray system.

This disclosure provides embodiments of a combined calibration object that can be used for both x-ray systems and optical systems.

SUMMARY

In one aspect there is disclosed a calibration object for an x-ray system and an optical system, the calibration object comprising:
a first part made of a first material having a matte surface, the first material having a first attenuation coefficient of x-rays;
a second part made of a second material having a second attenuation coefficient of x-rays different from the attenuation coefficient of the first material;
wherein the first part is attached to the second part so that one or more features are detectable by one or more optical cameras.

Accordingly, it is thus possible to use the same calibration object for both the x-ray system and any optical systems associated therewith. The optical systems may for example be a face scanner and/or motion compensation technology used in conjunction with CBCT scanners, as described in published application WO2016139347. This enables a one-button calibration so that the user does not have to change calibration object for each system that needs calibration.

In some embodiments, the features detectable by one or more cameras are holes in the first part of the calibration object.

In this way, the optical cameras can see both the first part, and the second part through the holes in the first part of the calibration object. The holes may be any geometric shape, for example square, elliptical, triangular, circular etc.

In some embodiments, the calibration object is constructed such that the difference in attenuation coefficients of x-rays between the first material and the second material is selected to provide results in a contrast of at least 0.1.

In order for the calibration object to be useful for calibration of the x-ray system, it is important that the contrast in x-ray attenuation between the first and second materials used is high enough to make a robust determination of the position of the calibration object.

In some embodiments, the second material comprises a glass substrate.

Glass substrates substantially allow x-rays to pass without being absorbed, so are a natural choice for the second material when producing a calibration object with a large enough contrast in x-ray wavelengths. Also, it is a relatively cheap material that produces a stable base for the calibration object.

The glass substrate may be between 2 mm and 10 mm thick. It is important to keep the weight of the calibration object down, as well as the cost of producing the calibration object. This may be achieved by having a relatively thin glass plate as the base of the calibration object. Preferably, the glass substrate may be around 4 mm thick, since this turns out to be a good compromise between being as thin as possible without being liable to break or bend or warp during production or in use.

In some embodiments, the glass substrate has a black surface. This ensures that there is a large contrast in the optical wavelengths between the first and second materials of the calibration object, so that the calibration object is more easily detectable by optical cameras.

In some embodiments the glass substrate is coated with diamond like carbon or black chromium coating.

By coating the glass substrate, the surface of the glass substrate will appear black. It is important to have as smooth a surface as possible, and therefore materials such as diamond like carbon are particularly suitable. In particular, diamond like carbon produces a very uniform, black and diffuse background.

In some embodiments the first material comprises perforated sheet metal.

Sheet metal has a relatively high attenuation of x-rays and will therefore provide a large contrast in x-ray wavelengths to the second material. By being perforated, i.e. having one or more holes, the sheet metal will allow optical cameras to view the second material, such as a glass substrate, through the sheet metal.

The sheet metal should preferably be between 50 microns and 1 mm thick. Of course, it is possible to have a thicker sheet of metal, Again, the thicker the material is, the more it will block the x-rays from passing through, and therefore provide a higher contrast. Conversely, the thinner it is, the cheaper it will be to produce, and the lighter it will be. A good compromise between these considerations is a thickness between 100 and 200 microns, preferably around 150 microns. Also, if the material becomes too thin it will be more likely to warp, for example during handling or environment changes such as humidity or temperature changes.

In some embodiments, steel is used for the first material. Steel is easily available and easy to work with.

In some embodiments the surface of the sheet metal is flash-etched. Flash-etching the surface of the sheet metal will give the sheet metal a matte surface, so that there is less risk of specular reflection for the optical cameras. In other words, etching the sheet metal allows good optical contrast to the black background regardless of the viewing angle.

In some embodiments, the sheet metal is glued onto the glass substrate. By gluing the first and second materials together, the calibration object can be handled as one piece.

In some embodiments, the sheet metal is laminated onto the glass substrate using an adhesive foil. Laminating is an alternative to gluing. Depending on the configuration of the calibration object and available production apparatus, one or the other method of attaching the two materials together may be preferable. For example, if gluing the perforated sheet onto the glass substrate, glue may leak out into the holes of the perforated sheet thereby changing the optical characteristics of the underlying glass substrate. Conversely, it may be difficult to create an adhesive foil that exactly matches the holes in the perforated sheet metal, so that in assembling the calibration object, a part of the adhesive foil may obscure the holes in the perforated sheet metal.

In some embodiments, the holes or perforations in the sheet metal are filled. Many materials may be used to fill the perforations, for example epoxy or polyurethane glue. By filling the holes in the perforated sheet metal after the sheet metal and glass substrate have been glued or laminated together, the top surface of the object will be flat. I.e. there will be no holes in the calibration object. This means that the determination by the optical cameras of the position of the holes now filled, will be more accurate.

In some embodiments the surface of the calibration object is ground and/or lapped. By grinding the surface of the calibration object, any overflow of material from the holes onto the sheet metal can be removed. And by lapping the calibration object, the surface will become very flat, within only a few microns. In these embodiments, the sheet metal does not necessarily need to be flash-etched, although it may still be done, since by carefully selecting the compound used in the lapping process according to known processes, the matte surface can be achieved.

BRIEF DESCRIPTION OF THE DRAWINGS

The above and/or additional objects, features and advantages of the present invention, will be further described by the following illustrative and non-limiting detailed description of embodiments of the present invention, with reference to the appended drawing(s), wherein.

DETAILED DESCRIPTION

In the following description, reference is made to the accompanying figures, which show by way of illustration how the invention may be practiced.

Figure 1:
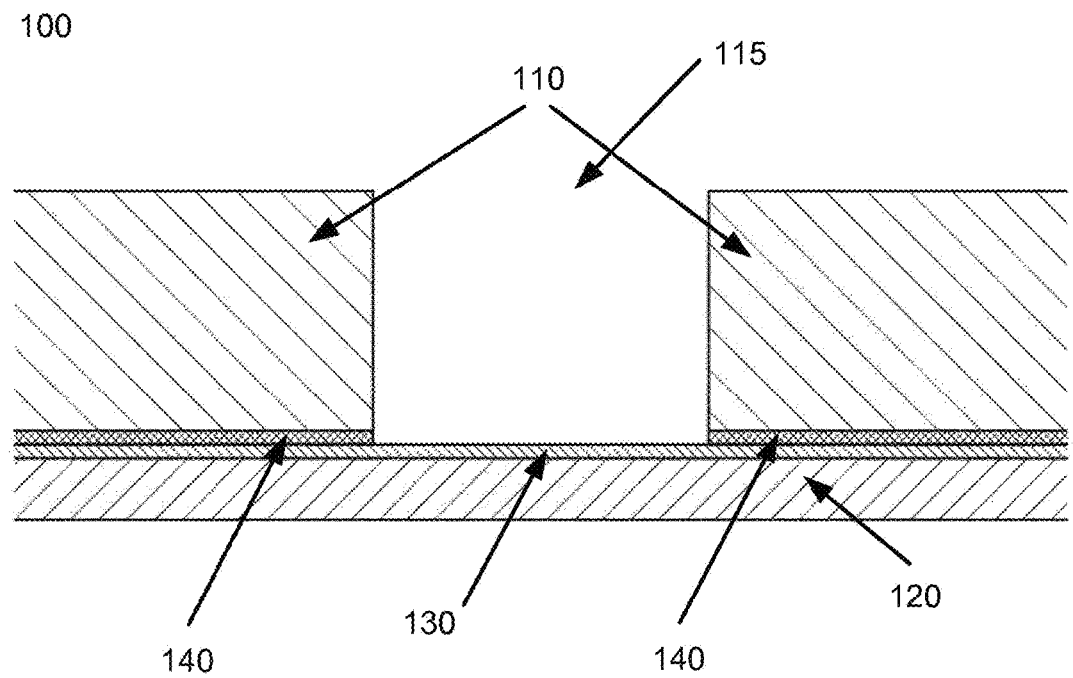
FIG. 1 shows a calibration object according to a first embodiment of this disclosure.

An embodiment of this disclosure is shown in FIG. 1. This embodiment shows a calibration object 100 for an x-ray system and any associated optical systems. The calibration object comprises a first part 110 having a matte surface. The first part 110 has holes 115. The first part 110 may be for example a perforated sheet of metal, such as steel. The first part 110 should have a matte surface. This ensures that the surface of the first part can be more easily detected by optical cameras, since it diminishes or eliminates the risk of specular reflection. If the first part 110 is made of metal such as steel, one advantageous way to achieve the matte surface is by flash-etching the metal sheet. The calibration object further comprises a second part 120, which may be for example a glass substrate. Of particular importance is the fact that the first and second parts are made of materials having different attenuation coefficients for x-rays, so that the calibration object can be used for calibrating the x-ray system. The glass substrate may comprise a coating 130. This coating may be for example diamond like carbon or thin black chromium, using well known lithographic processes which provides a very high accuracy. The coating is important to provide contrast in the calibration object, so that the position of the holes 115 can be more easily identified by optical cameras. The coating should preferably also be matte. The first part 110 may be attached to the second part 120 using glue/adhesive film 140. Using a glue has the advantage of being simple, although there is a possibility of glue being pushed out into the opening 115, thereby partly obscuring the coating 130. It may be easier to construct an adhesive film with holes corresponding to the holes in the metal part 110, but it may be more difficult to avoid the film being placed slightly inaccurately so that part of the adhesive film obscures the holes 115. One way of avoiding this, may be to create the adhesive film with holes having a larger size than the holes 115 in the first part 110.

Figure 2:
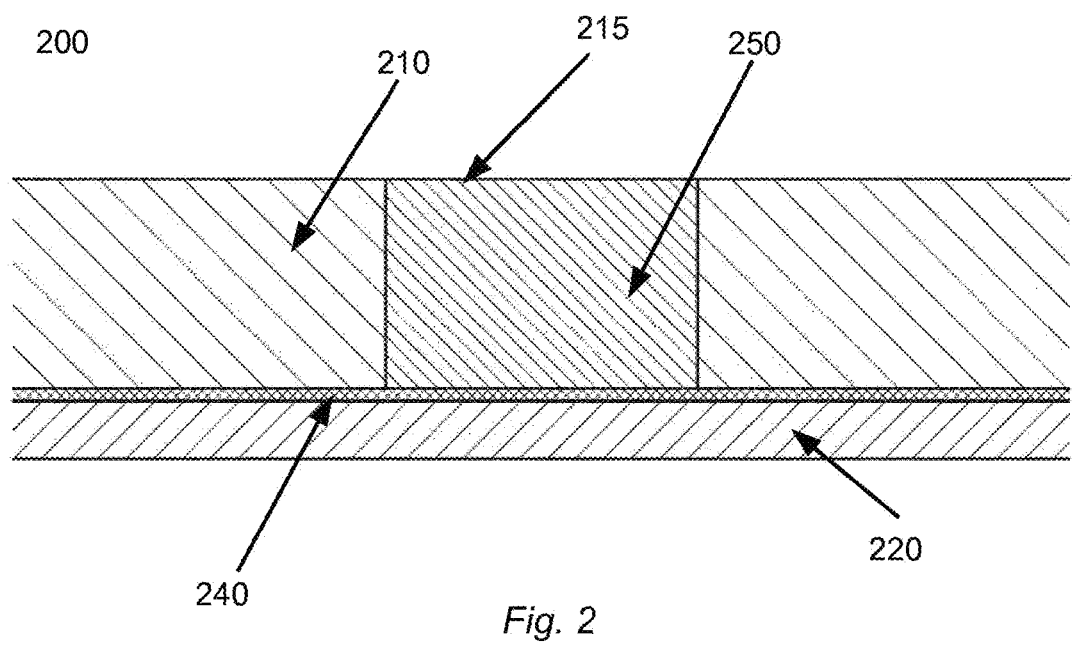
FIG. 2 shows a calibration object according to a second embodiment of this disclosure.

Another embodiment of the disclosure is shown in FIG. 2. The calibration object 200 again comprises a first part 210 and a second part 220. Here, the first part 210 may again be for example a perforated sheet of metal such as steel. The second part 220 may again be a glass substrate. It is important that the first part 210 and the second part 220 are made of materials having different attenuation coefficients for x-rays, so that the calibration object can be used to calibrate an x-ray system. The first part 210 and the second part 220 may be attached to each other using for example glue or an adhesive film. In this embodiment, the holes 215 in the first part 210 are filled in using for example black epoxy 250. The black epoxy has a large optical contrast to the second part, so that filled in holes have a much more well defined edge for the optical systems to calibrate on. After filling the holes with epoxy, the surface of the calibration object may be grounded and/or lapped. This will create a smooth and matte surface.

For both embodiments, the accuracy of the placement of the holes or dots in the calibration object comes from glass masters used for photoetching the metal plates. These masters are made using known lithographical processes having high resolution and accuracy, which translates into a very accurate calibration object.

Figure 3:
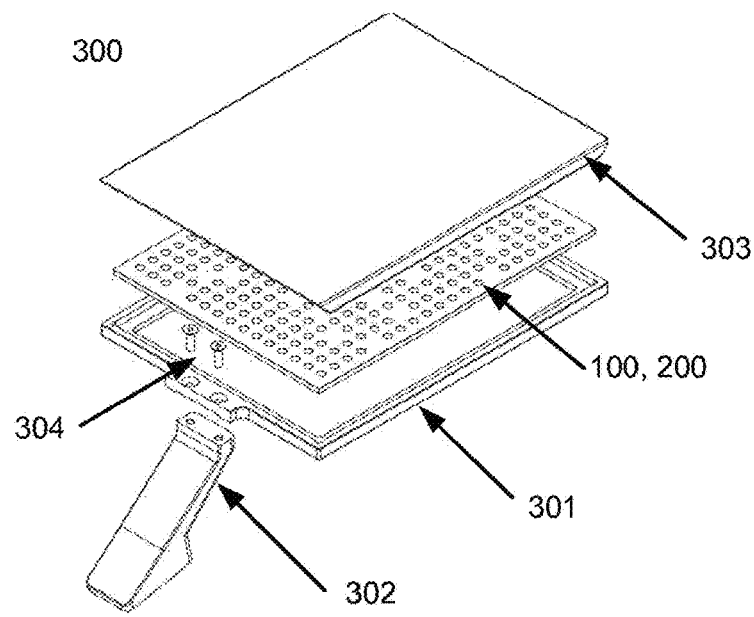
FIG. 3 shows a frame for calibration objects according to embodiments of this disclosure which may be used to attach the calibration object to an x-ray system.

FIG. 3 shows a frame 300 for calibration objects according to this disclosure. The calibration object 100, 200 as described above, needs to be put in a frame 300 so that the calibration object can be placed in the x-ray scanning system. The frame may comprise a frame piece 301 made of a material such as plastic which allows x-rays to pass through it. The frame may also comprise a handle 302 and fastening means 304 such as screws. The frame may further comprise a cover 303, made for example from a clear see through plastic.

Figure 4:
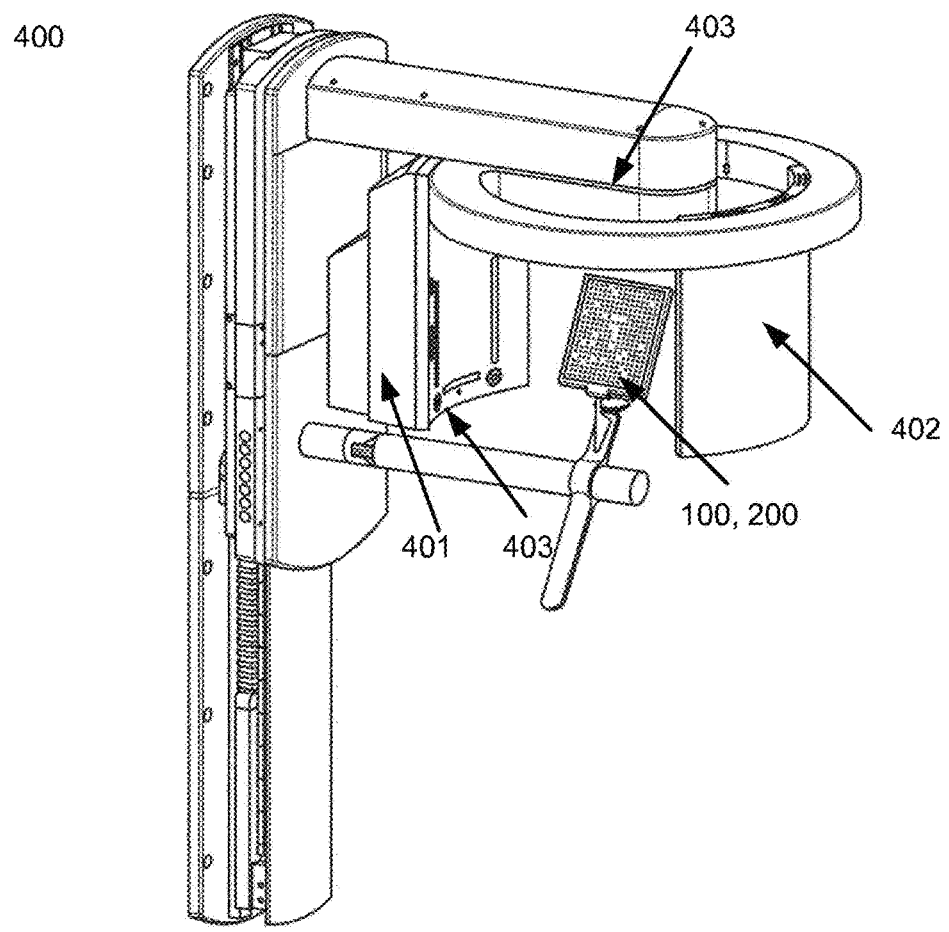
FIG. 4 shows a CBCT system according to embodiments of this disclosure.

FIG. 4 shows an x-ray system 400 according to embodiments of this disclosure. The x-ray system may be for example a panoramic or cephalometric x-ray scanner, or as shown in this case, a cone beam computed tomography scanner. The x-ray system comprises an x-ray source 401, an x-ray sensor 402 and one or more optical cameras 403. The calibration object as described above can then be placed in the imaging volume of the x-ray system as well as optical systems such as a face scanner or motion compensation system.

Although some embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

The term "obtaining" as used in this specification may refer to physically acquiring for example medical images using a medical imaging device, but it may also refer for example to loading into a computer an image or a digital representation previously acquired.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hard-wired circuitry instead of software or in combination with software.

EMBODIMENTS

1. A calibration object for an x-ray system and an optical system, the calibration object comprising:
    a first part made of a first material having a matte surface, the first material having a first attenuation coefficient of x-rays;
    a second part made of a second material having a second attenuation coefficient of x-rays different from the attenuation coefficient of the first material;
    wherein the first part is attached to the second part so that one or more features are detectable by one or more optical cameras.

2. The calibration object according to embodiment 1, wherein the difference in attenuation coefficients of x-rays between the first material and the second material is selected to provide a contrast of at least 0.1.

3. The calibration object according to any of the preceding embodiments, wherein the second material comprises a glass substrate.

4. The calibration object according to embodiment 3, wherein the thickness of the glass substrate is between 2 mm and 10 mm, preferably around 4 mm.

5. The calibration object according to any one or more of embodiments 3-4, wherein the glass substrate has a black surface.

6. The calibration object according to any of embodiments 3-5, wherein the glass substrate is coated with diamond like carbon.

7. The calibration object according to any of embodiments 3-5, wherein the glass substrate is coated with a black chromium coating.

8. The calibration object according to any of the preceding embodiments, wherein the first material comprises perforated sheet metal.

9. The calibration object according to embodiment 8, wherein the thickness of the sheet metal is between 50 microns and 1 mm.

10. The calibration object according to embodiment 8-9, wherein the thickness of the sheet metal is between 100 and 200 microns, preferably around 150 microns.

11. The calibration object according to any one or more of embodiments 8-10, wherein the sheet metal is made of steel.

12. The calibration object according to any one or more of embodiments 8-11, wherein the surface of the sheet metal is flash-etched.

13. The calibration object according to any one or more of embodiments 8-12, wherein the sheet metal is glued onto the glass substrate.

14. The calibration object according to any one or more of embodiments 8-12, wherein the sheet metal is laminated on the glass substrate using an adhesive foil.

15. The calibration object according to any one or more of embodiments 8-14, wherein the perforations in the sheet metal are filled with epoxy or polyurethane glue.

16. The calibration object according to the previous embodiment, wherein the epoxy or polyurethane glue is black.

17. The calibration object according to embodiment 15 or 16, wherein the surface of the calibration is ground and/or lapped.

18. A scanning system comprising:
    an x-ray source and an x-ray sensor;
    one or more optical cameras;
    a calibration object according to any of embodiments 1-18.

19. A method of manufacturing a calibration object for an x-ray system, the method comprising the steps of:
    flash-etching a perforated metal sheet; and
    laminating or gluing the perforated metal sheet on a glass substrate.

20. The method according to embodiment 19, wherein the holes in the perforated metal sheet are filled with epoxy or polyurethane glue after the perforated sheet metal has been glued or laminated on the glass substrate.

21. The method according to the previous embodiment, the method further comprising the steps of:
    grinding the surface of the calibration object after the holes in the perforated metal sheet are filled; and
    lapping the surface of the calibration object.

The invention claimed is:
1. A calibration object for an x-ray system and an optical system, the calibration object comprising:
    a first part made of a first material having a matte surface, the first material having a first attenuation coefficient of x-rays;
    a second part made of a second material having a second attenuation coefficient of x-rays different from the attenuation coefficient of the first material;

wherein the first part is attached to the second part so that one or more features are detectable by one or more optical cameras.

2. The calibration object according to claim 1, wherein the second material comprises a glass substrate.

3. The calibration object according to claim 2, wherein the thickness of the glass substrate is between 2 mm and 10 mm.

4. The calibration object according to claim 2, wherein the glass substrate is coated with diamond like carbon.

5. The calibration object according to claim 2, wherein the thickness of the glass substrate is around 4 mm.

6. The calibration object according to claim 1, wherein the first material comprises perforated sheet metal.

7. The calibration object according to claim 6, wherein the thickness of the sheet metal is between 100 and 200 microns.

8. The calibration object according to claim 6, wherein the surface of the sheet metal is flash-etched.

9. The calibration object according to claim 6, wherein the sheet metal is glued onto the glass substrate.

10. The calibration object according to claim 6, wherein the perforations in the sheet metal are filled with epoxy or polyurethane glue.

11. The calibration object according to claim 10, wherein the epoxy or polyurethane glue is black.

12. The calibration object according to claim 6, wherein the thickness of the sheet metal is around 150 microns.

13. The calibration object according to claim 1, wherein the difference in attenuation coefficients of x-rays between the first material and the second material is selected to provide a contrast of at least 0.1.

14. A scanning system comprising:
an x-ray source and an x-ray sensor;
one or more optical cameras;
a calibration object according to claim 1.

15. The calibration object according to claim 1, wherein the calibration object is a combined calibration object that is configured to be used to calibrate both the x-ray system and the optical system.

16. A method of manufacturing a calibration object for an x-ray system, the method comprising the steps of:
flash-etching a perforated metal sheet; and
laminating or gluing the perforated metal sheet on a glass substrate.

17. The method according to claim 16, wherein holes in the perforated metal sheet are filled with epoxy or polyurethane glue after the perforated sheet metal has been glued or laminated on the glass substrate.

18. The method according to claim 17, the method further comprising the steps of:
grinding the surface of the calibration object after the holes in the perforated metal sheet are filled; and
lapping the surface of the calibration object.

* * * * *